(12) United States Patent
Baker, Jr.

(10) Patent No.: US 7,039,538 B2
(45) Date of Patent: May 2, 2006

(54) PULSE OXIMETER WITH SEPARATE ENSEMBLE AVERAGING FOR OXYGEN SATURATION AND HEART RATE

(75) Inventor: Clark R. Baker, Jr., Castro Valley, CA (US)

(73) Assignee: Nellcor Puritant Bennett Incorporated, Pleasanton, CA (US)

( * ) Notice: Subject to any disclaimer, the term of this patent is extended or adjusted under 35 U.S.C. 154(b) by 0 days.

(21) Appl. No.: 10/796,578

(22) Filed: Mar. 8, 2004

(65) Prior Publication Data

US 2005/0197793 A1 Sep. 8, 2005

(51) Int. Cl.
*A61B 5/00* (2006.01)

(52) U.S. Cl. .......................... 702/78; 600/323; 600/528

(58) Field of Classification Search .................. 702/66, 702/78, 75, 76; 600/309, 310, 322, 323, 600/330, 331, 336, 473, 476, 528; 356/39–41
See application file for complete search history.

(56) References Cited

U.S. PATENT DOCUMENTS

| | | | | |
|---|---|---|---|---|
| 4,407,290 A | * | 10/1983 | Wilber | 600/330 |
| 4,911,167 A | | 3/1990 | Corenman et al. | |
| 4,928,692 A | * | 5/1990 | Goodman et al. | 600/324 |
| 4,960,126 A | * | 10/1990 | Conlon et al. | 600/336 |
| 5,743,263 A | * | 4/1998 | Baker, Jr. | 600/324 |
| 6,035,223 A | * | 3/2000 | Baker, Jr. | 600/323 |
| 6,293,915 B1 | * | 9/2001 | Amano et al. | 600/501 |
| 6,339,715 B1 | * | 1/2002 | Bahr et al. | 600/323 |
| 6,647,280 B1 | * | 11/2003 | Bahr et al. | 600/323 |
| 6,711,425 B1 | * | 3/2004 | Reuss | 600/331 |
| 6,760,609 B1 | * | 7/2004 | Jacques | 600/331 |
| 2002/0045806 A1 | | 4/2002 | Baker, et al. | |
| 2002/0099281 A1 | * | 7/2002 | Bahr et al. | 600/323 |
| 2002/0151812 A1 | * | 10/2002 | Scheiner et al. | 600/528 |
| 2003/0109776 A1 | * | 6/2003 | Jacques | 600/331 |
| 2003/0144584 A1 | * | 7/2003 | Mendelson | 600/323 |
| 2004/0034293 A1 | * | 2/2004 | Kimball | 600/323 |

OTHER PUBLICATIONS

International Search Report for PCT/US2005/007388, dated Jun. 14, 2005 (6 pages).

* cited by examiner

*Primary Examiner*—Carol S. W. Tsai
(74) *Attorney, Agent, or Firm*—Fletcher Yoder PC (57) ABSTRACT

The use of two separate ensemble averagers for processing a detected waveform for use in calculating oxygen saturation and a pulse rate. The ensemble averager used for calculating oxygen saturation operates on a signal which has been normalized, while the ensemble averager for the pulse rate calculation operates on a signal which has not been normalized. The metrics chosen for the two paths through the two ensemble averagers can be varied to optimize the ensemble averaging for oxygen saturation or pulse rate calculations.

14 Claims, 4 Drawing Sheets

FIG. 3 Composite Pulses are updated by averaging input samples with the existing Composite Pulse samples

FIG. 4 Example of the Ensemble Averaging subsystem's variable weighting

FIG. 6 State Machine for Updating Buffer Indices, i_Idx and j_Idx.

FIG. 7 State Machine for Updating First Pulse in Composite Pulse Buffers

FIG. 5 State Machine for Updating Second Pulse in Composite Pulse Buffers

PULSE OXIMETER WITH SEPARATE ENSEMBLE AVERAGING FOR OXYGEN SATURATION AND HEART RATE

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention relates to oximeters, and in particular to ensemble averaging of pulses in a detected waveform from a pulse oximeter.

Pulse oximetry is typically used to measure various blood chemistry characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed at various wavelengths is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

N-100. The N-100 technology, dating to around 1985, accepted or rejected pulses based on pulse history of the size of pulses, pulse shape, expected time to occur (frequency) and ratio of R/IR.

In particular, the N-100 found pulses by looking for a signal maximum, followed by a point of maximum negative slope, then a minimum. The processing was done in a state machine referred to as "munch." Each maximum was not qualified until the signal passed below a noise threshold, referred to as a noise gate. This acted as an adaptive filter since the noise gate level was set by feedback from a subsequent processing step to adapt to different expected signal amplitudes. The pulses are then accepted or rejected in a "Level3" process which was a filter which adapts to changing signals by comparing the amplitude, period and ratio-of-ratios (ratio of Red to IR, with Red and IR being expressed as a ratio of AC to DC) of a new pulse to the mean of values in a history buffer, then determining if the difference is within a confidence level. If the new pulse was accepted, the history buffer was updated with the values for the new pulse. The level3 process acted as an adaptive bandpass filter with center-frequency and bandwidth (confidence limits) being adapted by feedback from the output of the filter.

N-200. The N-200 improved on the N-100 since it could be synchronized with an ECG, and included ECG filtering. The N-200 also added interpolation to compensate for baseline shift between the time of measuring the pulse maximum and minimum. The N-200 included other filtering features as well, such as a "boxcar" filter which computed the mean of a varying number of signal samples.

The N-200, after various filtering and scaling steps, applies the digitized signals to a "boxcar" filter, which computes the mean of N samples, where N is set by feedback from a subsequent processing step according to the filtered heart rate. New samples are averaged into the boxcar filter, while the oldest samples are dropped. The boxcar length (N) is used to set three parameters: a pulse threshold, absolute minimum pulse and small pulse. An ensemble-averaging (a.k.a "slider") filter then produces a weighted average of the new samples and the previous ensemble-averaged sample from one pulse-period earlier. The samples are then passed to a "munch" state machine and a noise gate, like the N-100. An interpolation feature is added to the N-100 process, to compensate for changes in the baseline level. Since the minimum and maximum occur at different times, a changing baseline may increase or decrease the minimum and not the maximum, or vice-versa.

"Ensemble averaging" is an integral part of C-Lock, which is NELLCOR's trademark for the process of averaging samples from multiple pulses together to form a composite pulse. This process is also known as "cardiac-gated averaging." It requires a "trigger" event to mark the start of each pulse.

Conlon U.S. Pat. No. 4,690,126 discloses ensemble averaging where different weights are assigned to different pulses and a composite, averaged pulse waveform is used to calculate oxygen saturation. The N-100 described above is described in U.S. Pat. No. 4,802,486. Aspects of the N-200 are described in U.S. Pat. No. 4,911,167 (Corenman) and U.S. Pat. No. 5,078,136 (Stone).

BRIEF SUMMARY OF THE INVENTION

The present invention is directed to the use of two separate ensemble averagers for processing a detected waveform for use in calculating oxygen saturation and a pulse rate. The ensemble averager used for calculating oxygen saturation operates on a signal which has been normalized, while the ensemble averager for the pulse rate calculation operates on a signal which has not been normalized. Note that the waveforms corresponding to both wavelengths must be normalized by the same quantity, such as the IR pulse amplitude, so as to preserve the ratio-of-ratios for oxygen saturation computation.

The use of a signal without normalization for the pulse rate improves the software's ability to disqualify artifacts that are substantially larger than physiological pulses, such as motion artifact. The use of a signal without normalization for the pulse rate avoids a pulse being missed due to normalization.

The metrics chosen for the two paths through the two ensemble averagers can be varied to optimize the ensemble averaging for oxygen saturation or pulse rate calculations. For example, a lower threshold is used for a metric to detect arrhythmic pulses when used to calculate pulse rate, as compared to calculating oxygen saturation. Also, a metric for a short term pulse amplitude ratio will be small when motion artifact has just subsided, and this is given more weight in the pulse rate calculation than in the oxygen saturation calculation (the short-term pulse amplitude ratio is current pulse amplitude/previous pulse amplitude).

DETAILED DESCRIPTION OF THE INVENTION

Figure 1:
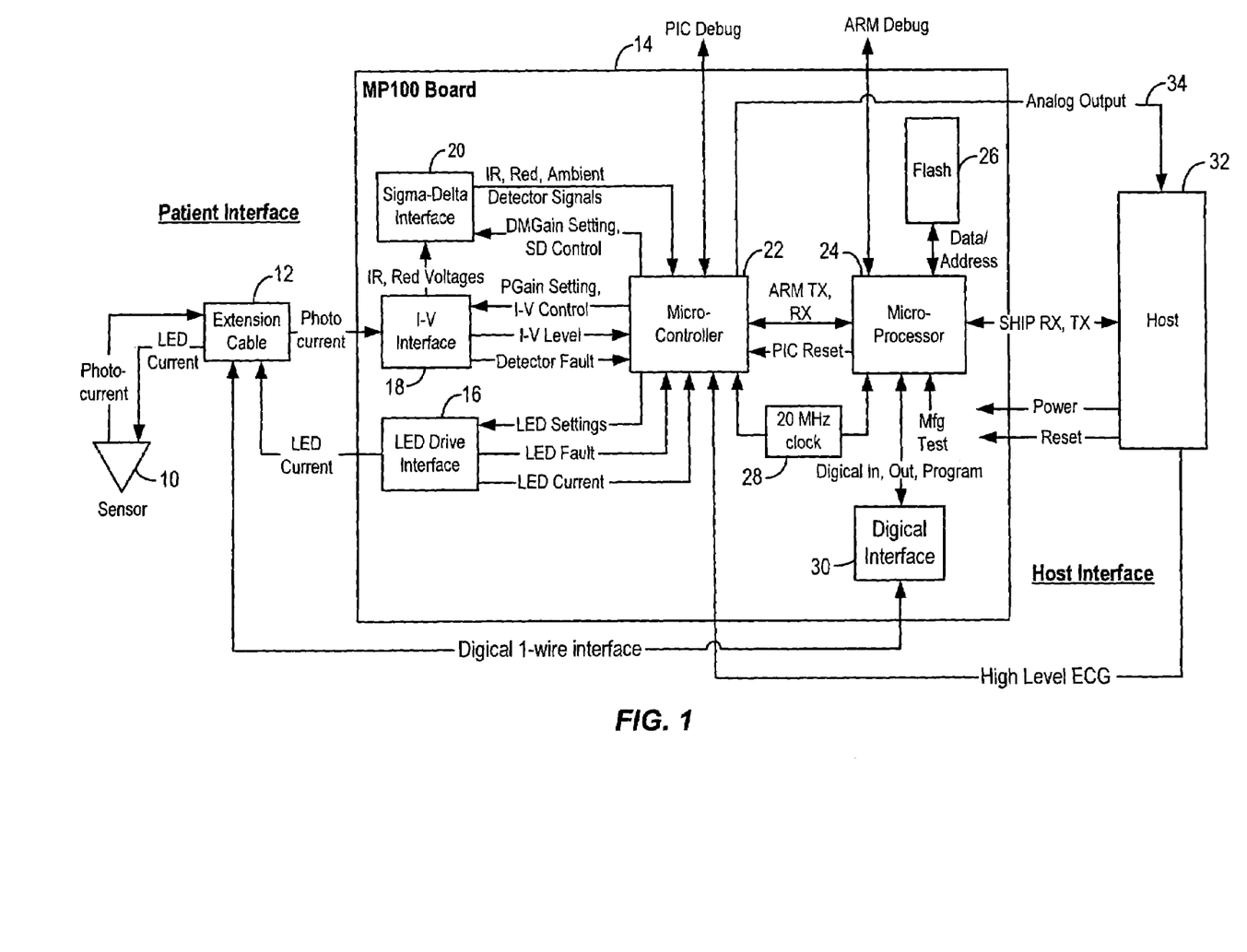
FIG. 1 is a block diagram of an oximetry system incorporating an embodiment of the invention.

FIG. 1 illustrates an embodiment of an oximetry system incorporating the present invention. A sensor 10 includes red and infrared LEDs and a photodetector. These are connected by a cable 12 to a board 14. LED drive current is provided by an LED drive interface 16. The received photocurrent from the sensor is provided to an I-V interface 18. The IR and red voltages are then provided to a sigma-delta interface 20 incorporating the present invention. The output of sigma-delta interface 20 is provided to a microcontroller 22 which includes a 10-bit A/D converter. Controller 22 includes flash memory for a program, and EEPROM memory for data. The processor also includes a controller chip 24 connected to a flash memory 26. Finally, a clock 28 is used and an interface 30 to a digital calibration in the sensor 10 is provided. A separate host 32 receives the processed information, as well as receiving an analog signal on a line 34 for providing an analog display.

Design Summary The design of the present invention is intended to deal with unwanted noise. Signal metrics are measured and used to determine filter weighting. Signal metrics are things that indicate if a pulse is likely a plethysmograph or noise, such as frequency (is it in the range of a human heart rate), shape (is it shaped like a heart pulse), rise time, etc. A similar technique was used in the Nellcor N200, described in the background of this application. The new design adds a number of different features and variations, such as the use of two ensemble averagers as claimed in the present invention.

Figure 2:
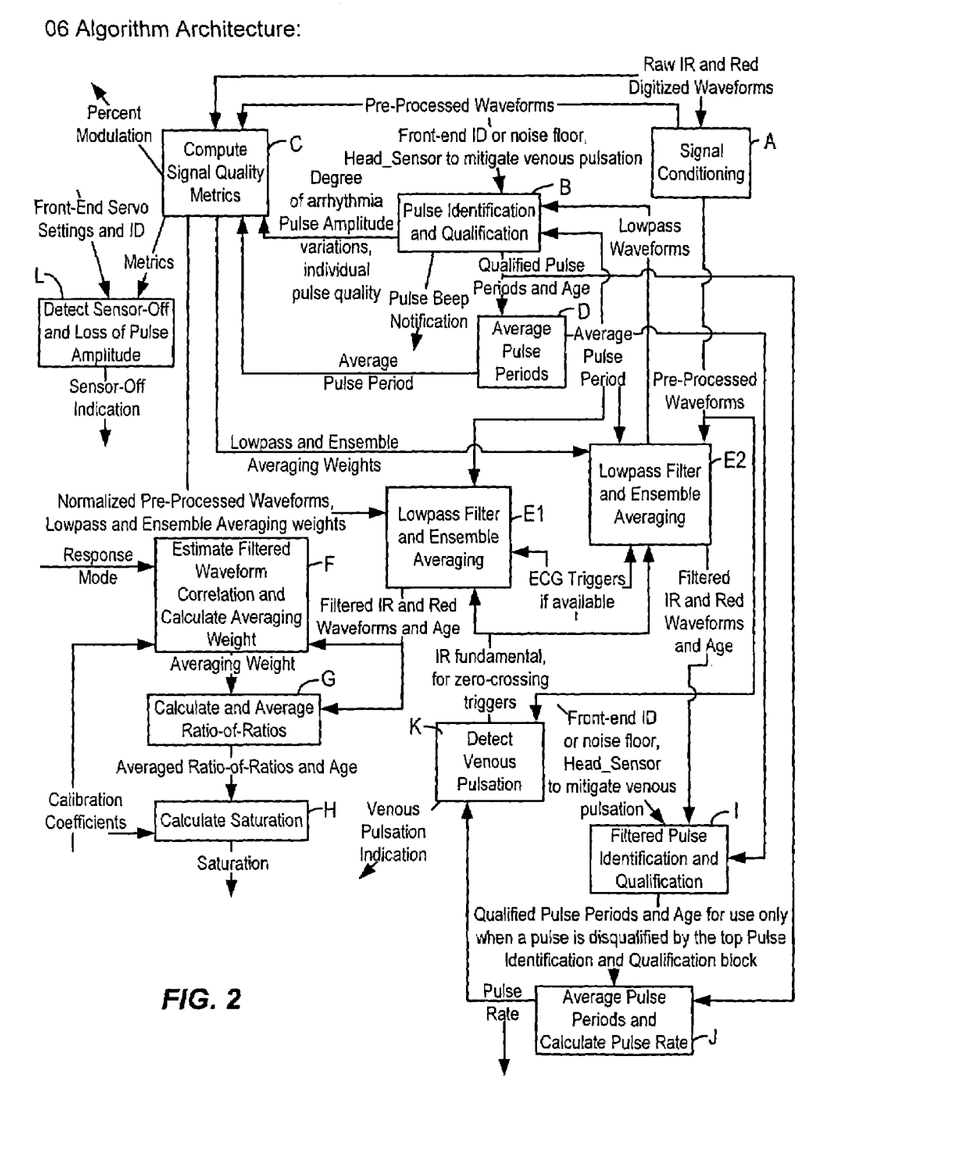
FIG. 2 is a diagram of the software processing blocks of an oximeter including an embodiment of the present invention.

Details of the architecture are shown in the diagram of FIG. 2. This design calculates both the oxygen saturation, and the pulse rate, which are described separately below.

I. Oxygen Saturation Calculation

A. Signal Conditioning—The digitized red and IR signals are received and are conditioned in this block by (1) taking the 1st derivative to get rid of baseline shift, (2) low pass filtering with fixed coefficients, and (3) dividing by a DC value to preserve the ratio. The function of the Signal Conditioning subsystem is to emphasize the higher frequencies that occur in the human plethysmograph and to attenuate low frequencies in which motion artifact is usually concentrated. The Signal Conditioning subsystem selects its filter coefficients (wide or narrow band) based on hardware characteristics identified during initialization.
Inputs—digitized red and IR signals
Outputs—Pre-processed red and IR signals B. Pulse Identification and Qualification—The low pass filtered and digitized red and IR signals are provided to this block to identify pulses, and qualify them as likely arterial pulses. This is done using a pre-trained neural network, and is primarily done on the IR signal. The pulse is identified by examining its amplitude, shape and frequency, just as was done in the Nellcor N-100. An input to this block is the average pulse period from block D. This function is similar to the N-100, which changed the upfront qualification using the pulse rate. The output indicates the degree of arrhythmia and individual pulse quality.
Inputs—(1) Pre-processed red and IR signals, (2) Ave. pulse period, (3) Lowpass Waveforms from the low pass filter.
Outputs—(1) Degree of arrhythmia, (2) pulse amplitude variations, (3) individual pulse quality, (4) Pulse beep notification, (5) qualified pulse periods and age.

C. Compute Signal Quality Metrics—This block determines the pulse shape (derivative skew), period variability, pulse amplitude and variability, Ratio of Ratios variability, and frequency content relative to pulse rate.
Inputs—(1) raw digitized red and IR signals, (2) degree of arrhythmia, individual pulse quality, pulse amplitude variation (3) pre-processed red and IR signals, (4) average pulse period.
Outputs—(1) Lowpass and ensemble averaging filter weights, (2) metrics for sensor off detector, (3) Normalized Pre-processed waveforms, (4) percent modulation.

D. Average Pulse Periods. This block calculates the average pulse period from the pulses received.
Inputs—Qualified pulse periods and age.
Outputs—Average pulse period.

E1. Lowpass Filter and Ensemble Averaging—Block E1 low pass filters and ensemble averages the signal conditioned by block A, and normalized by block C, for the pulse rate identification. The weights for the low pass filter are determined by the Signal Metrics block C. The signal is also ensemble averaged (this attenuates frequencies other than those of interest near the pulse rate and its harmonics), with the ensemble averaging filter weights also determined by Signal Metrics block C. Less weight is assigned if the signal is flagged as degraded. More weight is assigned if the signal is flagged as arrhythmic because ensemble-averaging is not appropriate during arrhythmia. Red and IR are processed separately, but with the same filtering weights. The filtering is delayed approximately one second to allow the signal metrics to be calculated first.

The filters use continuously variable weights. If samples are not to be ensemble-averaged, then the weighting for the previous filtered samples is set to zero in the weighted average, and the new samples are still processed through the code. This block tracks the age of the signal—the accumulated amount of filtering (sum of response times and delays in processing). Too old a result will be flagged (if good pulses haven't been detected for awhile).
Inputs—(1) normalized pre-processed red and IR signals, (2) average pulse period, (3) low pass filter weights and ensemble averaging filter weights, (4) ECG triggers, if available, (5) IR fundamental, for zero-crossing triggers.

Outputs—(1) filtered red and IR signals, (2) age.

F. Estimate Filtered Waveform Correlation and Calculate Averaging Weight—this uses a noise metric similar to that used in the N100 and N200 described above, and doesn't use feedback. The variable weighting for the filter is controlled by the ratio-of-ratios variance. The effect of this variable-weight filtering is that the ratio-of-ratios changes slowly as artifact increases and changes quickly as artifact decreases. The subsystem has two response modes. Filtering in the Fast Mode targets an age metric of 3 seconds. The target age is 5 seconds in Normal Mode. In Fast Mode, the minimum weighting of the current value is clipped at a higher level. In other words, a low weight is assigned to the newest ratio-of-ratios calculation if there is noise present, and a high weight if no noise is present.

Inputs—(1) filtered red and IR signals and age, (2) calibration coefficients, (3) response mode (user speed settings).

Outputs—averaging weight for ratio-of-ratios calculation.

H. Calculate Saturation—Saturation is calculated using an algorithm with the calibration coefficients and averaged ratio of ratios.

Inputs—(1) Averaged Ratio-of-Ratios, (2) calibration coefficients.

Outputs—Saturation.

II. Pulse Rate Calculation

E2. Lowpass Filter and Ensemble Averaging—Block E2 low pass filters and ensemble averages the signal conditioned by block A, for the pulse rate identification. The weights for the low pass filter are determined by the Signal Metrics block C. The signal is also ensemble averaged (this attenuates frequencies other than those of interest near the pulse rate and its harmonics), with the ensemble averaging filter weights also determined by Signal Metrics block C. Less weight is assigned if the signal is flagged as degraded. More weight is assigned if the signal is flagged as arrhythmic since filtering is not appropriate during arrhythmia. Red and IR are processed separately. The process of this block is delayed approximately one second to allow the signal metrics to be calculated first.

The filters use continuously variable weights. If samples are not to be ensemble-averaged, then the weighting for the previous filtered samples is set to zero in the weighted average, and the new samples are still processed through the code. This block tracks the age of the signal—the accumulated amount of filtering (sum of response times and delays in processing). Too old a result will be flagged (if good pulses haven't been detected for awhile).

Inputs—(1) pre-processed red and IR signals, (2) average pulse period, (3) Lowpass filter weights and ensemble averaging filter weights, (4) ECG triggers, if available, (5) IR fundamental, for zero-crossing triggers.

Outputs—(1) filtered red and IR signals, (2) age.

I. Filtered Pulse Identification and Qualification—This block identifies and qualifies pulse periods from the filtered waveforms, and its results are used only when a pulse is disqualified by block B.

Inputs—(1) filtered red and IR signals and age, (2) average pulse period, (3) hardware ID or noise floor, (4) kind of sensor.

Outputs—qualified pulse periods and age.

J. Average Pulse Periods and Calculate Pulse Rate—This block calculates the pulse rate and average pulse period.

Inputs—Qualified pulse periods and age

Outputs—(1) average pulse period, (2) pulse rate.

III. Venous Pulsation

K. Detect Venous Pulsation—Block K receives as inputs the pre-processed red and IR signal and age from Block A, and pulse rate and provides an indication of venous pulsation as an output. This subsystem produces an IR fundamental waveform in the time domain using a single-tooth comb filter which is output to the Ensemble Averaging filters.

Inputs—(1) filtered red and IR signals and age, (2) pulse rate.

Outputs—Venous Pulsation Indication, IR fundamental

IV. Sensor Off

L. Detect Sensor-Off and Loss of Pulse Amplitude—The Pulse Lost and Sensor Off Detection subsystem uses a pre-trained neural net to determine whether the sensor is off the patient. The inputs to the neural net are metrics that quantify several aspects of the behavior of the IR and Red values over the last several seconds. Samples are ignored by many of the algorithm's subsystems while the Signal State is not either Pulse Present or Sensor Maybe Off. The values of the Signal State variable are: "Pulse Present, Disconnect, Pulse Lost, Sensor Maybe Off, and Sensor Off."

Inputs—(1) metrics, (2) front-end servo settings and ID

Outputs—Signal state including sensor-off indication

Ensemble Averaging Subsystem

Ensemble Averaging subsystem. The function of the Ensemble Averaging subsystem is to filter its input streams with a variable weighting, and output waveforms that are less distorted by noise or motion artifact. Reducing the degree of artifact in the filtered waveforms enables a more robust saturation or rate estimate during motion or noise.

The Ensemble Averaging subsystem requires IR and Red inputs every sample that are zero-mean over the span of several pulses.

Input samples are first IIR lowpass filtered with a weight received from the Signal Metrics subsystem (LPF_Weight) and then stored in a one-second-delay buffer.

It averages the ith IR and Red samples of the current one-second delayed input pulse with the ith samples of the previous composite pulse to form the ith samples of the current composite pulse. The trigger to start the beginning of a pulse period is derived from (in order of priority) the RWave_Occurred input and the average period input (Optical_Period). The weight given to the current sample versus the corresponding sample of the previous pulse is determined by the value of Ensemble_Averaging_Weight value received from the Signal Metrics subsystem.

Figure 3:
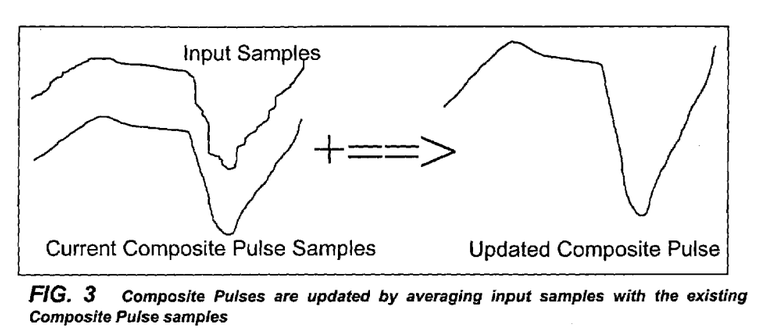
FIG. 3 is a diagram showing the creation of a composite pulse.

This composite pulse is less distorted by noise or motion artifact than the filter's input pulses. FIG. 3 is a conceptual illustration of how pulses are averaged together to form the composite pulse.

The subsystem receives and qualifies triggers, which should be synchronous with the heartbeat. The triggers are qualified R-Wave triggers from the R-wave Qualification subsystem when available. When R-Wave triggers are unavailable, the triggers are generated internally from the average period input from the Pulse Rate Calculation subsystem (Optical_Period). A "pulse" is considered to start at each qualified trigger and end at the next qualified trigger. In this way, consecutive triggers are used to define the ensemble averaging period.

Figure 4:
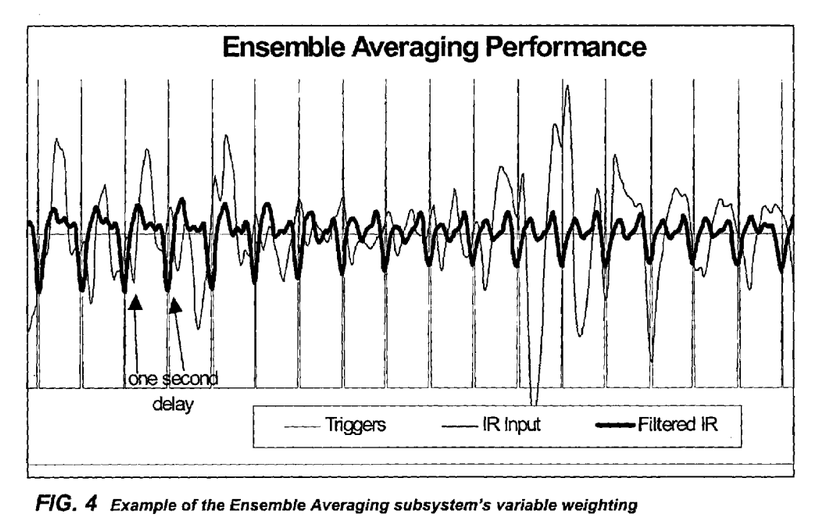
FIG. 4 is a chart of the ensemble averaging performance.

FIG. 4 shows a representation of the subsystem's response to a series of pulses corrupted by motion artifact. The vertical lines are R-Wave triggers. The filtered output restores the approximate shape and size of the input pulses. The amount of averaging increases as the motion artifact increases as determined by the Ensemble_Averaging-_Weight received from Signal Metrics subsystem.

FIG. 4 is an example of the Ensemble Averaging subsystem's variable weighting. R-Wave triggers mark the start of each pulse. The IR Input line shows pulses corrupted by motion artifact. The Filtered IR line is a composite of multiple pulses that largely restores the original pulse size and shape. Filtered IR is delayed by one second from the IR input.

Lowpass Filter—The IR and Red input waveforms are IIR filtered using a weight (LPF_Weight) received from the Signal Metrics subsystem as follows:

Lowpass_Waveforms$_t$=Lowpass_Waveforms$_{t-1}$+LPF-_Weight*(Input_Waveforms$_t$+Lowpass_Waveforms$_{t-1}$)

During subsystem initialization, the weight is set to a default of 1.0.

One-Second Delay Buffer—The IR and Red Lowpass_Waveforms (along with their associated age and status) and the RWave_Occurred input are stored in one-second long buffers (IR_Inputs, Red_Inputs, Input_Valid, Age_Inputs, RWave_Inputs).

Timestamp—The timestamp (Current_Time_ctr) is simply a 32-bit counter that is initialized to 0 and then incremented every sample period. Several received values are stored along with their timestamps in order to reconstruct their age.

Ensemble Weight Buffer—The last four Ensemble_Averaging_Weights received and their timestamps are stored in the Ensemble_Average_Buffer and the Ensemble_Weight_Timestamp. This allows every entry in the one-second delay buffers to be associated with its correct weight. Whenever delayed inputs are retrieved from the one-second delay buffers, the associated ensemble weight is set to the oldest weight in this buffer that is at least as recent as the delayed sample (weight timestamp+one second≧Current_Time_ctr).

Trigger Qualification—The subsystem selects its trigger from one of two inputs: RWave_Occurred or Optical_Period. RWave_Occurred is the default trigger. Before RWave_Occurred is used as a trigger, it passes through the one-second-delay buffer mentioned earlier in order to be synchronous with the delayed IR and red samples. Triggers based on Optical_Period input from the Pulse Rate Calculation subsystem are only qualified when R-Wave triggers have not been received for at least five seconds. This waiting period is deemed sufficient to determine that R-Wave triggers are unavailable. Then, the first trigger from the Optical_Period is delayed until the first zero-crossing of the subsystem's Optical_Trigger_WF input waveform. Subsequently, the trigger is derived solely from Optical_Period.

Ensemble Averaging Model—The subsystem receives IR and Red input samples and a trigger to indicate the start of each pulse. Note that the IR and Red inputs have already been lowpass filtered and passed through the one-second-delay buffer. It estimates the pulsatile component of its current input sample by averaging the ith sample of the current pulse with the ith sample of the previous estimated pulse.

The filter output is therefore a composite of multiple pulses, calculated as each sample is received. The filter has the frequency response of a comb filter that only passes frequencies at or near the pulse rate and its harmonics. The amount of averaging determines the width of the comb filter's "teeth".

The filter assumes that the ith sample value of the current pulse is roughly equal to the ith sample of the previous pulse. Note that i is a ramp function of time, t, that has a value of zero at each qualified trigger and increments at each subsequent sample.

Ensemble Averaging Filter Equations and Intermediate Variables—The Ensemble Averaging filter uses the Ensemble_Averaging_Weight, w, which is supplied by the Signal Metrics subsystem. The following equation shows the basic steps that must be performed at the ith sample of every pulse:

$$z_i = z'_i + w_t(x_t - z'_i) \tag{1}$$

where $z'_i$ denotes the value of $z_i$ from one pulse ago. $z_i$ is the ensemble-filtered output of the subsystem. All $z_i$s are stored in the Composite Pulse Buffer. $x_t$ is the most recent output sample from the one-second-delay buffer. All the variables in equation 1 are scalars.

Composite Pulse Buffers—The composite IR and Red pulses are stored in separate Composite Pulse Buffers. The index, i, is reset to the start of the buffers when a trigger is received and then incremented for each sample.

The buffers must be long enough to store one 20 BPM pulse plus a 10 percent margin to allow for pulse-rate variability. Therefore, the buffers are updated with at least 1.1 consecutive composite pulses at 20 BPM and two composite pulses at most pulse rates. If i should go past the end of the buffer, normal processing must be suspended until the next trigger, during which time the filter's outputs will be set identical to its inputs.

When the interval between triggers gets longer, the Composite Pulse Buffers may not contain recent samples to average at the end of a pulse.

The jth sample of the composite pulse is calculated each sample, where j=i+m and m is the number of samples between the current and previous qualified triggers, i.e the pulse period. Note that j, like i, is a ramp function of t.

For j, equation (1) is modified to read:

$$z^j = z'_j + w_t(x_t - z_j') \tag{1b}$$

The same value of w is used to calculate $z_i$ and $z_j$. When j reaches the end of the buffer, calculation of $z_j$ must be suspended until j becomes valid again.

Changing pulse periods might cause small discontinuities in the subsystem output after each trigger is received. Special processing during the first four samples after a trigger reduces this effect. The filtered output sample is interpolated between the standard output (equation 1) and the second composite pulse (equation 1b), so that the filtered output is respectively 80%, 60%, 40%, and 20% of $z_j$ on these samples. If the second composite pulse is not available, the input waveform is used in its place.

Initialization, Reinitialization, Clearing and Ignored Samples—Until two triggers plus one second samples have been received, j is meaningless and $z_j$ is not calculated.

The subsystem contains two methods to recover from an interruption in processing. When more than five seconds elapse between triggers, the subsystem is "cleared" at the next qualified trigger. The clearing operation sets all of the subsystem's persistent variables to their initial values, with the exception of the following variables that are essential to trigger qualification and maintaining the one-second-delay buffers:

1. The subsystem's current timestamp.
2. The elapsed times since the last R-wave trigger and the last qualified trigger.
3. The previous Optical_Trigger_Waveform sample, used to detect zero crossings.
4. The state of the Trigger Qualification State Machine.
5. One-second delay input buffers
6. Ensemble_Averaging_Weight buffer This "clearing" operation is performed because this condition should be rare and may indicate a lengthy interruption in processing. The filter outputs are also identical to the filter inputs whenever i overflows the end of the Composite Pulse buffer.

When a sample is ignored (not processed) due to lack of valid input for periods under five seconds, the Composite Pulse Buffer is left unchanged and the subsystem's outputs are marked Invalid. When processing resumes and if Optical_Period is non-zero, the buffer's indices are reset to what they should have been an integral number of pulse periods ago and the one-second-delay buffers are reset. This is done because the Composite Pulse Buffer should still contain an accurate representation of current pulses after a brief interruption in processing. The subsystem is "cleared" if the Optical_Period estimate is zero (invalid) or samples are ignored for at least five seconds. Most "ignored samples" are expected to be due to the adjustments in the oximeter's LED brightness or amplifier gain, which generally take less than two seconds. The equations for resetting the indices are as follows:

Elapsed_Periods=int(Interruption_Duration/Optical_Period)

Samples_In_Fractional_Period=Interruption_Duration_Elapsed_Periods*Optical_Period New_Idx=round(i_Idx+Samples_In_Fractional_Period) or if New_Idx≧Optical_Period, New_Idx=round(i_Idx+Samples_In_Fractional_Period—Optical_Period)

j=New_Idx+j−i_Idx, provided j has not already overflowed, and would not overflow, the Composite Pulse Buffer.

i_Idx=New_Idx, provided i_Idx has not already overflowed, and would not overflow, the Composite Pulse Buffer.

The Ensemble Averaging subsystem is reinitialized when the Pulse Lost and Sensor Off Detection subsystem determines that a pulse has been re-acquired after being absent for a prolonged period of time, or when a sensor is connected. "Reinitialization" means that ALL of the subsystem's persistent variables are set to their initial values. This is done because both of the events that invoke reinitialization make it likely that the Ensemble Averaging subsystem's previous pulse representation is no longer current.

The elapsed time intervals since the last R-wave and the last qualified trigger are incremented on ignored samples. R-Waves or zero-crossings that occur during ignored samples are not used to qualify triggers.

Figure 5:
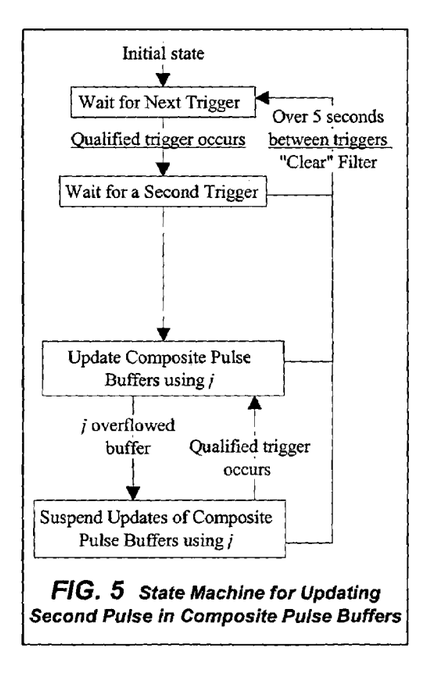
FIGS. 5–7 are diagrams of state machines for updating certain variables in a composite pulse buffer.
Figure 6:
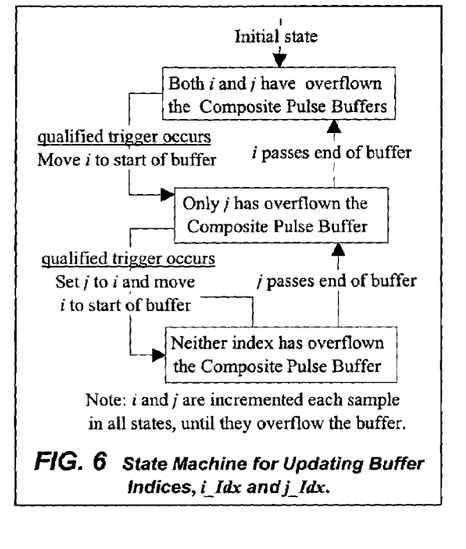
Figure 7:
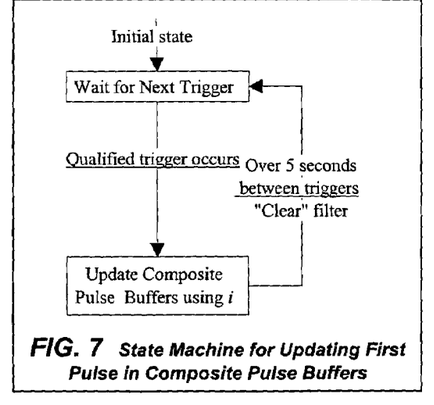

The state transition diagrams of FIGS. 5–7 show the state machines for updating each of the two pulses maintained in the Composite Pulse Buffers and their indices.

Age Metric—The subsystem receives the age in samples, $Age\_Inputs_i$, of its IR and Red inputs and outputs the age, $Age\_Out_i$, of its composite pulse outputs. For each sample, $Age\_Out_i$, is incremented by the elapsed time since it was last updated and then averaged with $Age\_Inputs_i$, using the filter weight (Ensemble_Averaging_Weight), w, used to update the composite waveforms. The formula for $Age\_Out_i$ is:

$$age\_out_i = age\_out_i + m + w_i((age\_in_i + N) - (age\_out_i + m))$$

where m is the number of samples since $Age\_Out_i$ was last updated and N is the number of samples in one second. The timestamp at which each $Age\_Out_j$ is updated must be stored in order to calculate m.

The subsystem must also update $Age\_Out_j$. The formula for $Age\_Out_j$ is as above, except that j is substituted for i.

The subsystem must increment a current timestamp (Current_Time_Ctr) every sample, including ignored samples.

When the subsystem is cleared or reinitialized, all entries in the Age_Out buffer are reinitialized to $Age\_Inputs_i$. Furthermore, all entries in the buffer for the timestamps at which the Age_Out entries were updated are set to the current timestamp minus 1. These steps are taken to assure that the Age_Out values are no older than the elapsed time since the subsystem was cleared or reinitialized.

The Ensemble Averaging instance whose waveforms are used for pulse qualification and pulse rate uses Rate_LPF_Weight, which depends solely on frequency content. The Ensemble Averaging instance whose waveforms are used to calculate ratio-of-ratios and saturation uses Sat_LPF_Weight, which also depends on whether the RoR_Variance metric would be better (lower) with the addition of lowpass filtering. These weights will range between 0.1 and 1.0, and will not increase more than 0.05 in any single step.

Ensemble Averaging Weights

When the subsystem is notified that the Pulse Identification and Qualification subsystem has just completed evaluation of a potential pulse, the subsystem updates ensemble-averaging weights, used by the instances of the Ensemble Averaging subsystem. Separate weights are computed for the two Ensemble Averaging instances whose outputs are used in computing saturation and pulse rate. These weights are based in part on metrics provided by the instance of the Pulse Identification and Qualification subsystem whose input waveforms have NOT been ensemble averaged.

The equations for Sat_Ensemble_Averaging_Filter_Weight are as follows:

x=max(Short_RoR_Variance, Pulse_Qual_RoR_Variance/1.5)*max(Long_Term_Pulse_Amp_Ratio, 1.0)

RoR_Variance_Based_Filt_Wt=0.5*0.05/max(0.05, x)

Arr_Prob=(Period_Var−0.1*Short_RoR_Variance−0.09)/(0.25−0.09);

Arr_Min_Filt_Wt_For_Sat=0.05+0.5*bound(Arr_Prob, 0, 1.0)

Sat_Ensemble_Averaging_Filter_Weight=max(RoR_Variance_Based_Filt_Wt, Arr_Min_Filt_Wt_For_Sat)*(1.0+Pulse_Qual_Score)

Sat_Ensemble_Averaging_Filter_Weight=min(Sat_Ensemble_Averaging_Filter_Weight, 1.0)

where bound (a, b, c) denotes min(max(a, b), c).

The above equations result in a default weight of 0.5 for low values of the Ratio-of-Ratios variances. Short_RoR_Variance and Pulse_Qual_RoR_Variance are both computed over a three-second interval. The interval for Pulse_Qual_RoR_Variance ends with the qualification or rejection of the most recent pulse, which would usually include the most recent samples. The weight is reduced by high Ratio-of-Ratios variances, and by high values of Long_Term_Pulse_Amp_Ratio that would typically indicate motion artifact. Arr_Min_Filt_Wt_For_Sat imposes a minimum value on the ensemble-averaging weight (range 0.05–0.55) based primarily on Period_Var, which quantifies the degree of arrhythmia. This is done because ensemble-averaging is not effective for pulses having dissimilar periods. If the most recent pulse received a good Pulse_Qual_Score, this can increase the maximum value of Sat_Ensemble_Averaging_Filter_Weight from 0.5 to 1.0.

The equations for Rate_Ensemble_Averaging_Filter_Weight are as follows:

Arr_Prob=(Period_Var−0.07)/(0.20−0.07)

Arr_Min_Filt_$Wt$_For_Rate=0.05+0.5*bound(Arr_Prob, 0, 1.0)

x=max(RoR_Variance_Based_Filt_$Wt$, Arr_Min_Filt_$Wt$_For_Rate)*(1.0+Pulse_Qual_Score)

if Short_Term_Pulse_Amp_Ratio*Long_Term_Pulse_Amp_Ratio<1.0 x=x/Short_Term_Pulse_Amp_Ratio if Avg_Period>0 x=x*bound
(Pulse_Qual_Score*Qualified_Pulse_Period/
Avg_Period, 1.0, 3.0)
Rate_Ensemble_Averaging_Filter_Weight=min
(x, 1.0)

These equations differ from the ones for Sat_Ensemble_Averaging_Filter_Weight as follows:
a) The thresholds used to compute Arr_Prob are somewhat lower, because it is desirable that arrhythmic pulses not be obscured by ensemble averaging prior to pulse qualification.
b) Small values of Short_Term_Pulse_Amp_Ratio typically indicate that motion artifact has just subsided, which means that the ensemble-averaging weight may be quickly increased. This has been found empirically to be beneficial for pulse qualification, but not for ratio-of-ratios filtering and saturation computation.
c) If the heart skips a beat, with or without prior arrhythmia, the longer-than-average Qualified_Pulse_Period that results will increase the ensemble-averaging weight, so as not to obscure the skipped beat from subsequent pulse qualification.

Definitions:

Data Inputs

Avg_Period—Average pulse period reported by Pulse Rate Calculation subsystem

Long_Term_Pulse_Amp Ratio—Quantifies last pulse amplitude compared to historic pulse amplitude. Provided by the Pulse Identification and Qualification subsystem. Values substantially larger than 1.0 are typically indicative of motion artifact, and result in lower Ensemble_Averaging_Filter_Weights.

Period_Var—Period-variability metric from the Pulse Identification and Qualification subsystem. Used to gauge the extent of arrhythmia.

Pulse_Qual_RoR_Variance—RoR_Variance metric from the Pulse Identification and Qualification subsystem. For instance, a value of 0.10 would indicate that the average difference between consecutive pulse periods is 10% of Avg_Period.

Pulse_Qual_Score—Score computed by the pulse qualification neural net in the Pulse Identification and Qualification subsystem. Zero is extremely poor and 1.0 is excellent.

Qualified_Pulse_Period—Most recent pulse period qualified by the Pulse Identification and Qualification subsystem.

Short_Term_Pulse_Amp_Ratio—Quantifies last pulse amplitude compared to previous pulse amplitude.

Outputs

Frequency_Ratio—Ratio of Mean_IR_Frequency_Content to pulse rate.

LPF_RoR_Variance—Quantifies variability of ratio-of-ratios. Computed over a 9-second window from LPF_Scaled_Waveforms.

Rate_LPF_Weight—Lowpass filter weight to be used by the instance of the Ensemble Averaging subsystem that preprocesses waveforms used for pulse qualification and pulse rate calculation.

RoR_Variance—Quantifies variability of ratio-of-ratios. Computed over a 9-second window from Scaled_Waveforms. A value of 0.10 would indicate that sample-to-sample ratio-of-ratios values differ from the mean ratio-of-ratios value by an average of 10% of the mean ratio-of-ratios value.

Sat_Ensemble_Averaging_Filter_Weight—Ensemble-averaging weight to be used by the instance of the Ensemble Averaging subsystem that preprocesses waveforms used for pulse qualification and pulse rate calculation.

Sat_LPF_Weight—Lowpass filter weight to be used by the instance of the Ensemble Averaging subsystem that preprocesses waveforms used for pulse qualification and pulse rate calculation.

Scaled_Waveforms—Scaled versions of IR and Red Pre_Processed_Waveforms.

Short_RoR_Variance—Quantifies variability of ratio-of-ratios. Computed over a 3-second window from Scaled_Waveforms.

Internal Variables

Arr_Prob—Likelihood of arrhythmia that would limit the amount of ensemble averaging. Based on Period_Var, with threshold that are specific to each of the two Ensemble_Averaging_Filter_Weights.

Arr_Min_Filt_Wt_For_Rate, Arr_Min_Filt_Wt_For_Sat—Minimum values for the two Ensemble_Averaging_Filter_Weights, based on their respective Arr_Prob values.

LPF_Scaled_Waveforms—Lowpass-filtered version of Scaled_Waveforms, used to compute LPF_RoR_Variance.

Mean_IR_Frequency_Content—Estimate of the mean frequency content of the IR input waveform.

RoR_Variance_Based_Filt_W—Component for Ensemble_Averaging_Filter_Weights based on RoR_Variance metrics and Long_Term_Pulse_Amp_Ratio.

What is claimed is:

1. A method for processing signals in a pulse oximeter to determine oxygen saturation and pulse rate, comprising:
receiving waveforms corresponding to two different wavelengths of light from a patient; ensemble averaging the waveforms in a first ensemble averager using variable weights;
calculating a pulse rate based on an output of the first ensemble averager; selecting first metrics for the first ensemble averager to optimize calculating the pulse rate;
normalizing the waveforms to produce normalized waveforms;

ensemble averaging the normalized waveforms in a second ensemble averager using variable weights;
calculating an oxygen saturation based on an output of the second ensemble averager; and
selecting second metrics for the second ensemble averager to optimize calculating the oxygen saturation.

2. The method of claim 1 wherein the first and second metrics both include an arrhythmia metric for detecting an arrhythmic pulse, the arrhythmia metric for the first metrics, in connection with calculating the pulse rate, having a lower associated threshold for recognizing arrhythmia than the arrhythmic metric for the second metrics.

3. The method of claim 1 wherein the first and second metrics both include a short term metric which is a measure of short-term changes in pulse amplitude;
the first ensemble averager increasing an ensemble averaging weight in response to a short-term decrease in pulse amplitude faster than the second ensemble averager.

4. A pulse oximeter for determining oxygen saturation and pulse rate, comprising:
a detector configured to receive waveforms corresponding to two different wavelengths of light from a patient;
a first ensemble averager configured to average the waveforms;
a pulse rate calculator, configured to calculate a pulse rate based on an output of the first ensemble averager;
a normalizer configured to normalize the waveforms to produce normalized waveforms;
a second ensemble averager configured to average the normalized waveforms;
an oxygen saturation calculator configured to calculate an oxygen saturation based on an output of said second ensemble averager; and
a signal quality metric calculator configured to provide first metrics for the first ensemble averager to optimize calculating the pulse rate, and second metrics for the second ensemble averager to optimize calculating the oxygen saturation, wherein the ensemble averagers are configured to ensemble average using variable weights.

5. A method for processing signals in a pulse oximeter to determine oxygen saturation and pulse rate, comprising:
receiving waveforms corresponding to two different wavelengths of light from a patient;
low pass filtering the waveforms in a first low pass filter;
calculating a pulse rate based on an output of the first low pass filter;
normalizing the waveforms to produce normalized waveforms;
low pass filtering the normalized waveforms in a second low pass filter,
calculating an oxygen saturation based on an output of the second low pass filter;
selecting first metrics for the first low pass filter to optimize the calculating the pulse rate; and
selecting second metrics for the second low pass filter to optimize calculating the oxygen saturation.

6. The method of claim 5 wherein:
the low-pass filtering weight associated with the first low pass filter is based on a frequency ratio metric which quantifies the frequency-content of the waveforms relative to a pulse-rate estimate.

7. The method of claim 5 wherein:
a low-pass filtering weight for the second low pass filter is based on
a frequency ratio metric which quantifies the frequency-content of the waveforms relative to a pulse-rate estimate that metric, and
a separate Ratio-of-Ratios variance metric.

8. A method for processing signals in a pulse oximeter to determine oxygen saturation and pulse rate, comprising:
receiving waveforms corresponding to two different wavelengths of light from a patient;
low pass filtering and ensemble averaging the waveforms in a first low pass filter and ensemble averager;
calculating a pulse rate based on an output of the first low pass filter and ensemble averager;
normalizing the waveforms to produce normalized waveforms;
low pass filtering and ensemble averaging the normalized waveforms in a second low pass filter and ensemble averager; and
calculating an oxygen saturation based on an output of the second low pass filter and ensemble averager.

9. A pulse oximeter for determining oxygen saturation and pulse rate, comprising:
a detector which receives waveforms corresponding to two different wavelengths of light from a patient;
a first low pass filter configured to filter the waveforms;
a pulse rate calculator, configured to calculate a pulse rate based on an output of the first low pass filter;
a normalizer configured to normalize the waveforms to produce normalized waveforms;
a second low pass filter configured to filter the normalized waveforms;
an oxygen saturation calculator configured to calculate an oxygen saturation based on an output of the second low pass filter; and
a signal quality metric calculator configured to provide first metrics for the first low pass filter to optimize calculating the pulse rate, and second metrics for the second low pass filter to optimize calculating the oxygen saturation, wherein the low pass filters are configured to ensemble average using variable weights.

10. The pulse oximeter of claim 9 wherein:
the low-pass filtering weight associated with the first low pass filter is based on a frequency ratio metric which which quantifies the frequency-content of the waveforms relative to a pulse-rate estimate.

11. The pulse oximeter of claim 9 wherein:
a low-pass filtering weight for the second low pass filter is based on
a frequency ratio metric which which quantifies the frequency-content of the waveforms relative to a pulse-rate estimate that metric, and
a separate Ratio-of-Ratios variance metric.

12. A pulse oximeter for determining oxygen saturation and pulse rate, comprising:
a detector which receives waveforms corresponding to two different wavelengths of light from a patient;
a first low pass filter and ensemble averager configured to filter and to average the waveforms;
a pulse rate calculator, configured to calculate a pulse rate based on an output of the first low pass filter and ensemble averager;
a normalizer configured to normalize the waveforms to produce normalized waveforms;
a second low pass filter and ensemble avenger configured to filter and to average the normalized waveforms; and
an oxygen saturation calculator configured to calculate an oxygen saturation based on an output of the second low pass filter and ensemble averager.

13. A method for processing signals in a pulse oximeter to determine oxygen saturation, comprising:
   receiving waveforms corresponding to two different wavelengths of light from a patient;
   processing a new waveform after a pulse period trigger to ensemble average with a historical average waveform; and
   when the new waveform differs from the historical average waveform by more than a predetermined threshold, interpolating between the new waveform and the historical average waveform for a first few samples of a new, composite historical average waveform.

14. The method of claim 13 wherein the first few samples are four samples, and the interpolations are at 80%, 60%, 40%, and 20% of the difference between the new waveform and the historical average waveform.

* * * * *